United States Patent [19]

Faraj et al.

[11] Patent Number: 5,126,476
[45] Date of Patent: Jun. 30, 1992

[54] PROCESS FOR THE PREPARATION OF ARYL-, HETEROARYL-, OR CYCLOALKYL-SUBSTITUTED ALKYL URETHANES AND ISOCYANATES

[75] Inventors: Mahmoud K. Faraj, Newtown Square; Haven S. Kesling, Jr., Drexel Hill; John G. Zajacek, Devon, all of Pa.

[73] Assignee: Arco Chemical Technology, L.P., Wilmington, Del.

[21] Appl. No.: 646,535

[22] Filed: Jan. 25, 1991

[51] Int. Cl.$^5$ ............... C07C 269/00; C07C 271/16; C07C 261/02
[52] U.S. Cl. ............................ 560/24; 560/9; 560/24; 560/25; 560/28; 560/29; 560/32; 560/115; 560/345
[58] Field of Search ............ 560/24, 25, 9, 27, 28, 560/29, 32, 115, 345, 355, 357

[56] References Cited

U.S. PATENT DOCUMENTS

| | | | |
|---|---|---|---|
| 4,130,577 | 12/1978 | Nagato et al. | 260/453 |
| 4,439,616 | 3/1984 | Singh et al. | 560/25 |
| 4,570,012 | 2/1986 | Singh et al. | 560/25 |
| 4,871,871 | 10/1989 | Shawh et al. | 560/344 |
| 4,873,364 | 10/1989 | Shawh et al. | 560/344 |
| 4,879,410 | 11/1989 | Singh et al. | 560/344 |
| 4,883,908 | 11/1989 | Shawh et al. | 560/344 |

FOREIGN PATENT DOCUMENTS

| | | | |
|---|---|---|---|
| 1144564 | 10/1980 | Canada | 560/24 |
| 0164491 | 10/1983 | European Pat. Off. | 560/25 |

OTHER PUBLICATIONS

Krow et al *J. Chem. Eng. Data*, 17, p. 116 (1972).
Wilkens (Tetrahedron Letters (1965) 4817).
Murphy et al. (J. Chem. Soc., Perkin Trans. I (1981) 447).

*Primary Examiner*—Jose G. Dees
*Assistant Examiner*—B. Frazier
*Attorney, Agent, or Firm*—Jonathan L. Schuchardt

[57] ABSTRACT

A process for making aryl-, heteroaryl-, or cycloalkyl-substituted alkyl urethanes is disclosed. The urethanes are prepared by electrophilic carbamylation of aromatic compounds with alkylene bis(carbamic acid esters) or the equivalent in the presence of an acidic catalyst and a polar aprotic solvent. The alkyl urethanes may be cracked to give the corresponding substituted alkyl isocyanates.

26 Claims, No Drawings

PROCESS FOR THE PREPARATION OF ARYL-, HETEROARYL-, OR CYCLOALKYL-SUBSTITUTED ALKYL URETHANES AND ISOCYANATES

FIELD OF THE INVENTION

The invention relates to the field of aliphatic urethane synthesis. More specifically, a process for making aryl, heteroaryl, or cycloalkyl-substituted alkyl urethanes by carbamylation is disclosed. The urethanes can be thermally cracked to give aryl-, heteroaryl-, or cycloalkyl-substituted alkyl isocyanates (aliphatic isocyanates).

BACKGROUND OF THE INVENTION

Aliphatic isocyanates impart favorable ultraviolet-light stability to polyurethanes compared with the more conventional aromatic isocyanates. Unfortunately, aliphatic isocyanates are often difficult and costly to produce.

Aliphatic isocyanates are available from the reaction of aliphatic amines with phosgene. Phosgene is toxic, difficult to handle safely, and generates corrosive by-products. Non-phosgenation routes to isocyanates are therefore desirable.

U.S. Pat. No. 4,130,577, for example, teaches to prepare aliphatic isocyanates from the reaction of an alkali metal isocyanate with an alkyl halide precursor. Although high yields are possible, the slow rate of reaction and the halide by-product make this process and similar ones commercially unattractive.

An attractive route to aromatic isocyanates relies on thermal cracking of urethane precursors. When various reaction promoters are employed, the reaction rates and yields of isocyanates are favorable. Such processes are described in U.S Pat. Nos. 4,871,871, 4,873,364, and 4,883,908. A drawback of synthesizing isocyanates from urethanes is that the required urethane precursors are difficult to prepare from inexpensive, readily available feedstocks.

Krow et al. (*J. Chem. Eng. Data* 17 (1972) 116) describe the synthesis of benzyl urethanes from aryl ethers. A phenyl ether, such as anisole, is reacted with an equivalent of a 1,1-diurethane, such as methylene diurethane, in the presence of boron trifluoride etherate in refluxing toluene to give a benzylurethane; for example:

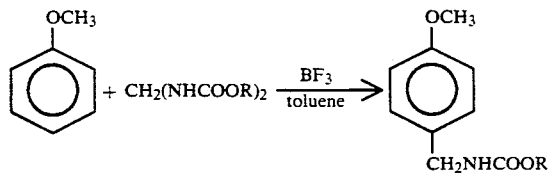

The poor-to-moderate yields reported (20-51%) are too low for the process to have commercial value. Also, there is no indication that the aromatic ring can be di- or polyalkylated by this method. The ability to introduce more than one urethane group on an aromatic ring is important because it allows for the synthesis of precursors to useful di- and polyisocyanates.

Merten et al. (Belgian Patent No. 627,280) teach (Example 5) that the reaction of phenol with 3.1 equivalents of methylene-bis-(ethyl carbamate) in toluene at 100° C. gives 2,4,6-tris(ethyl carbamylmethyl)phenol.

Singh et al. (U.S. Pat. No. 4,879,410) teach a process for preparing aralkyl mono- and diurethanes or ureas by carbamylmethylation or acid-catalyzed addition at 40° C.–b 100° C. of formaldehyde and esters of carbamic acid to aromatic hydrocarbons. The process comprises heating an aromatic hydrocarbon, a carbamate such as methyl carbamate, formaldehyde, and an acid catalyst to form the aryl-substituted alkyl urethane. The preferred catalysts are sulfuric and phosphoric acids. In general, the "catalyst" is present in excess and also serves as a solvent. Other optional solvents taught include protic solvents such as methanol, ethanol, and acetic acid, and halogenated hydrocarbons such as dichloromethane, ethylene dichloride, and chlorobenzene.

The key advantage of the Singh process is that valuable isocyanate precursors can be prepared from relatively inexpensive aromatic hydrocarbons. The process, however, suffers from several drawbacks: (1) Mineral acid solvents are commercially undesirable because they are corrosive and extremely costly to neutralize and dispose of properly; (2) Yields of the dicarbamates are typically quite low (about 10-45% with m-xylene, for example); and (3) A large proportion of the aromatic hydrocarbon is not converted to useful products.

A commercially viable non-phosgene route to aliphatic isocyanates is needed. Preferably, the process uses inexpensive, readily available feedstocks. Especially desirable is a process for preparing high yields of aliphatic urethane compounds (aliphatic isocyanate precursors), especially those with more than one urethane group in the molecule, without the corrosivity, waste treatment, and product-loss problems associated with the use of mineral acid solvents.

SUMMARY OF THE INVENTION

We have discovered a process for producing aryl- heteroaryl-, or cycloalkyl-substituted alkyl urethanes that overcomes many of problems of prior-art aliphatic urethane syntheses, a process that uses easily recoverable, non-corrosive solvents, and gives high yields of aliphatic urethanes.

In one embodiment of the invention, an aromatic ring-containing compound having at least one aromatic-ring hydrogen atom is reacted with either (a) an alkylene bis(carbamic acid ester) of the formula:

or (b) a formaldehyde source and a carbamic acid ester, in the presence of an acidic catalyst and a polar aprotic solvent to produce an aryl or heteroaryl-substituted alkyl urethane. At least one aromatic-ring hydrogen atom is replaced by a

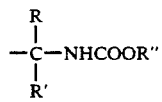

group in the aryl or heteroaryl-substituted alkyl urethane. R and R', which may be the same or different, are selected from the group consisting of hydrogen, $C_1$–$C_{30}$ alkyl, aryl, alkenyl, and aralkyl. R" is selected from the group consisting of $C_1$–$C_{10}$ and aryl. The polar aprotic solvent, which is a key element of the invention, is selected from the group consisting of $C_1$–$C_{10}$ aliphatic and aromatic nitriles, amides, phosphoramides, nitro compounds, and sulfoxides. The aromatic ring-containing compound is optionally substituted with one or more monovalent radicals selected from the group consisting of hydroxy, $C_1$-$C_{30}$ alkyl, alkaryl, aryl, amino, alkylthio, trialkylsilyl, acylamino, alkoxy, and alkoxyalkyl. In a second embodiment of the invention, the aryl or heteroaryl-substituted alkyl urethane is heated in the vapor phase or in a high-boiling solvent to thermally convert the

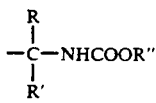

substituents of the urethane to

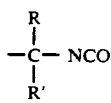

groups to produce an aryl or heteroaryl-substituted alkyl isocyanate.

In a third embodiment of the invention, the aryl-substituted alkyl urethane is catalytically hydrogenated, and the resulting cycloalkyl-substituted alkyl urethane is cracked to produce a cycloalkyl-substituted alkyl isocyanate.

DETAILED DESCRIPTION OF THE INVENTION

The aryl-, heteroaryl-, or cycloalkyl substituted alkyl urethanes produced by the process of the invention are derived from aromatic ring-containing compounds. At least one aromatic-ring hydrogen that can undergo substitution by a urethane group must be present. The aromatic ring-containing compound optionally has one or more substituents on the ring that are electron donating and can activate the ring toward electrophilic aromatic substitution. Thus, the aromatic ring-containing compound is optionally substituted with one or more monovalent radicals selected from the group consisting of hydroxy, $C_1$-$C_{30}$ alkyl, alkaryl, aryl, amino, alkylthio, trialkylsilyl, acylamino, alkoxy, and alkoxyalkyl.

Preferred aromatic ring-containing compounds, because they are inexpensive and readily available, are aromatic hydrocarbons such as benzene, toluene, xylenes, naphthalene, alkyl-substituted benzenes, biphenyl, diphenylmethane, and the like, polycyclic aromatic compounds such as anthracene, phenanthrene, and the like, and mixtures thereof. Also preferred are phenolic compounds, such as phenol, bisphenol-A, and the like, and aromatic ethers, such as anisole, diphenyl ether, ethyl phenyl ether, and the like. Mixtures of benzene ring-containing compounds may be employed, and such is likely because inexpensive aromatic feedstocks often contain a variety of different compounds having similar boiling points.

Preferred aromatic ring-containing compounds also include heteroaryl compounds such as furan, thiophene, pyridine, pyrrole, imidazole, indole, quinoline, and the like, and mixtures thereof.

Preferred aromatic-ring containing compounds for use in the process of the invention have the formula:

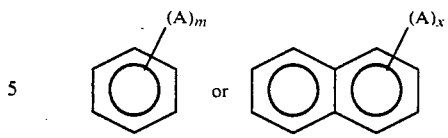

wherein A is a monovalent radical selected from the group consisting of hydroxy, $C_1$-$C_{30}$ alkyl, alkaryl, aryl, acylamino, amino, alkylthio, alkylsilyl, alkoxy, and alkoxyalkyl; m is an integer from 0 to 5; and x is an integer from 0 to 7.

Particularly preferred aromatic-ring compounds include benzene, toluene, xylenes, diphenylmethane, anisole, diphenyl ether, pyridine, thiophene, and furan.

Alkylene bis(carbamic acid esters) of the formula:

are reacted with the aromatic ring-containing compounds in the process of the invention to produce aryl or heteroaryl-substituted alkyl urethanes. In the formula, R and R', which may be the same or different, are selected from the group consisting of hydrogen, $C_1$-$C_{30}$ alkyl, alkenyl, aryl, and aralkyl. R" is selected from the group consisting of $C_1$-$C_{10}$ alkyl and aryl. Preferably, R and R' are selected from the group consisting of hydrogen, methyl, ethyl, phenyl, methylphenyl, vinyl, and alkylvinyl.

Examples of suitable alkylene bis(carbamic acid esters) include, but are not limited to, methylene bis(methyl carbamate) (MBM), methylene bis(ethyl carbamate), dimethylmethylene bis(methyl carbamate), methylphenylmethylene bis(methyl carbamate), and the like.

Instead of an alkylene bis(carbamic acid ester), a combination of a formaldehyde or acetaldehyde source and a carbamic acid ester may be used in the process of the invention. Any suitable source of formaldehyde or acetaldehyde may be used. For example, formalin, gaseous formaldehyde, acetaldehyde, paraformaldehyde, formaldehyde-alcohol complexes, and the like may be used. Carbamic acid esters of the formula $H_2N$-COOX may be used, in which X represents a $C_1$-$C_{10}$ alkyl, aryl, or aralkyl group. Examples of suitable carbamic acid esters that may be used in combination with the formaldehyde or acetaldehyde source include methyl carbamate, ethyl carbamate, phenyl carbamate, benzyl carbamate, isopropyl carbamate, and the like. Methyl carbamate and ethyl carbamate are preferred.

The amount of alkylene bis(carbamic acid ester) or aldehyde source/carbamic acid ester employed relative to the amount of aromatic ring-containing compound will depend on many factors, most importantly on the desired degree of ring alkylation. Typically, the amount will be within the range of about 0.2 to 10 equivalents of alkylene bis(carbamic acid ester) per equivalent of aromatic ring-containing compound.

The process of the invention is performed in the presence of an acidic catalyst. The catalyst may be a protic acid such as acetic, sulfuric, methanesulfonic, p-toluenesulfonic, phosphoric acid and the like, a Lewis acid such as boron trifluoride, boron trifluoride etherate, zinc chloride, and the like, or a solid acid, such as a sulfonic acid resin, perfluorinated sulfonic acid resin, acidified poly(vinylpyridine) resin, or acid clay. Lewis acids, such as boron trifluoride and boron trifluoride etherate, and sulfonic acid resins are particularly preferred. The amount of catalyst used varies depending on the type of catalyst used and the desired reaction rate. The amount of Lewis acid or protic acid used is preferably within the range of about 0.1 to 25 mole percent based on the amount of aromatic ring-containing compound. The amount of solid acid used in preferably within the range of about 0.2 wt. % to about 50 wt. % based on the total weight of the reactants.

The process of the invention is performed in the presence of a polar aprotic solvent selected from the group consisting of $C_1$-$C_{10}$ aliphatic and aromatic nitriles, amides, phosphoramides, nitro compounds, sulfones, and sulfoxides. Suitable polar aprotic solvents are those that have a dielectric constant within the range of about 10 to about 50. Examples of suitable polar aprotic solvents useful in the process of the invention include, but are not limited to, acetonitrile, propionitrile, benzonitrile, N,N-dimethylformamide, N,N-dimethylacetamide, N-methyl-2-pyrrolidone, hexamethylphosphoramide (HMPA), hexamethylphosphorus triamide (HMPT), nitromethane, nitrobenzene, nitroethane, dimethyl sulfoxide, sulfolane, and the like, and mixtures thereof. Particularly preferred polar aprotic solvents include acetonitrile, propionitrile, nitromethane, nitrobenzene, and nitroethane.

Any suitable amount of polar aprotic solvent may be used. It is generally preferred to use an amount of polar aprotic solvent within the range of about 5 weight percent to about 95 weight percent. For optimum results, however, it is preferred that a maximum of about 80 weight percent of the polar aprotic solvent be used.

The polar aprotic solvent is a key element in the process for the following reasons: (1) Compared with conventional hydrocarbon solvents, polar aprotic solvents greatly enhance the ability to dialkylate aromatic rings; (2) In contrast to the mineral acid solvents relied upon by other prior art processes, polar aprotic solvents are essentially non-corrosive and require no expensive neutralization and waste treatment; (3) Polar aprotic solvents are readily separated from the reaction products by distillation or other separation techniques; (4) product losses are minimized, with yields of useful products (usually mono- or dialkylated materials) typically greater than 90%.

The process of the invention may be performed in any suitable reaction vessel, and may be carried out batchwise or continuously. A preferred way to perform the process is simply to combine the aromatic ring-containing compound with the alkylene bis(carbamic acid ester) or equivalent, the polar aprotic solvent, and the acidic catalyst in a glass or metal reaction vessel equipped with agitating means, such as a mechanical stirring device, and to heat the reaction mixture to the desired temperature for a time sufficient to permit conversion of the aromatic ring-containing compound to an aryl or heteroaryl-substituted alkyl urethane. Conversion of the starting materials to products may be measured by any suitable means. Gas chromatography is often suitable for following disappearance of volatile starting materials. Product ratios (monocarbamate to dicarbamate, for example) may advantageously be determined by liquid chromatography or any other suitable technique.

The process of the invention may be performed at any desired reaction temperature. Preferably, reaction temperatures within the range of about 25° to 250° C. are employed. More preferably, the range of temperatures is about 50° C. to about 160° C. A particularly convenient temperature at which to perform the process is at the boiling point of the polar aprotic solvent.

The process of the invention may be performed at, above, or below atmospheric pressure, as desired. The process is optionally performed in an inert atmosphere of nitrogen, argon, or the like, as desired.

In a preferred embodiment of the invention, the aryl- or heteroaryl-substituted alkyl urethane produced as previously described is heated in the vapor phase or in a high-boiling solvent to thermally convert the urethane product to an aryl-or heteroaryl-substituted alkyl isocyanate. This reaction, which is known as "cracking," is advantageously performed in the presence of one or more reaction promoters. Any of the promoters known in the art may be used. Particularly preferred promoters include, but are not limited to, mineral acids, amines, amine halide salts, phosphorus pentoxide, sulfonic acids, and the like. If desired, the acidic catalyst may be removed from the urethane prior to the cracking step. The alcohol by-products from the cracking reaction may be recovered and reused.

In another embodiment of the invention, the aryl-substituted alkyl urethane is catalytically hydrogenated to produce a cycloalkyl-substituted alkyl urethane. In the hydrogenation process, the aryl-substituted alkyl urethane is combined with hydrogen and a catalyst at elevated pressure and under conditions effective to saturate the benzene ring. Any suitable catalyst known to those skilled in the art may be employed. Preferred catalysts are transition metals such as rhodium, ruthenium and the like. The resulting cycloalkyl-substituted alkyl urethane may then be cracked as described above to produce a cycloalkyl-substituted alkyl isocyanate.

The following examples are provided to illustrate the invention. Those skilled in the art will recognize numerous modifications that are within the scope and spirit of the invention.

EXAMPLES 1-7

Preparation of Aliphatic Urethanes from Anisole Using Boron Trifluoride Etherate Anisole (7 mmol) was combined with methylene bis(methyl carbamate) (21 mmol), 1,2-dichlorobenzene (130 mg—internal standard for gas chromatography), and the reaction solvent indicated in Table 1 (25 mL). Boron trifluoride etherate (0.7 mmol) was added, and the mixture was heated to reflux for the amount of time indicated in the table. The percent conversion of anisole was determined by gas chromatography. The selectivity to monocarbamate, dicarbamate, and unidentified condensation products (heavies) was determined by high-performance liquid chromatography (HPLC).

TABLE 1
Preparation of Aliphatic Urethanes from Anisole
Effect of Solvent on Reaction Rate and Selectivity
Boron Trifluoride Etherate Catalyst

| Ex | Solvent | Temp (°C.) | Time (h) | Percent Conv. | Selectivity (%) | | |
|---|---|---|---|---|---|---|---|
| | | | | | Monocarb | Dicarb | Heavies |
| C1 | Toluene | 110 | 5 | 51 | 71 | 4 | 25 |
| C2 | Toluene | 110 | 24 | 71 | 65 | 9 | 26 |
| C3 | None | 128 | 2 | 100 | trace | 60 | 40 |
| C4 | None | 100 | 4 | 100 | 40 | 54 | 6 |
| C5 | $C_2H_4Cl_2$ | 83 | 24 | 80 | 45 | 25 | 30 |
| 6 | nitromethane | 90 | 3 | 100 | <2 | 78 | 22 |
| 7 | acetonitrile | 83 | 4 | 100 | 12 | 76 | 12 |

As shown in Table 1 (Comparative Examples 1, 2, and 5), the use of an aromatic hydrocarbon solvent such as toluene or a chlorinated hydrocarbon such as 1,2-dichloroethane results in incomplete conversion of anisole (even after 24 hours) and poor selectivity to the desired dicarbamate product, even with 3 equivalents of methylene bis(methyl carbamate) per equivalent of anisole.

When the process is performed in the absence of a solvent (comparative Examples 3 and 4), reaction rates are favorable and good selectivity to the urethane products (94% mono- plus dicarbamate) is observed. Increasing the temperature to only 128° C., however, results in a large increase in the proportion of condensation by-products (40%).

When polar aprotic solvents are employed (Examples 6 and 7) reaction rates are favorable, as indicated by complete conversion within 4 hours. Selectivity and yields of the dicarbamate products are high (76-78%), and the proportion of condensation by-products is reduced.

These results highlight the advantage of using a polar aprotic solvent to optimize reaction rate and improve selectivity to the desired dicarbamate products.

EXAMPLES 8-10
Preparation of Aliphatic Urethanes from Anisole Using Sulfonic Acid Resins Anisole (7 mmol) was combined with methylene bis(methyl carbamate) (21 mmol), 1,2-dichlorobenzene (130 mg—internal standard for gas chromatography), and the reaction solvent indicated in Table 2 (25 mL). A sulfonic acid resin catalyst (identified in Table 2) was added, and the mixture was heated to reflux for the amount of time indicated in the table. The percent conversion of anisole was determined by gas chromatography. The selectivity to monocarbamate, dicarbamate, and unidentified condensation products (heavies) was determined by HPLC. The results obtained with boron trifluoride (Examples 6 and 7) are included in Table 2 for comparison.

TABLE 2
Preparation of Aliphatic Urethanes from Anisole
Effect of Catalyst on Reaction Rate and Selectivity

| Ex | Cat. | Solvent | Temp (°C.) | Time (h) | Percent Conv. | Selectivity | | |
|---|---|---|---|---|---|---|---|---|
| | | | | | | Monocarb | Dicarb | Heavies |
| 6 | $BF_3$ | $CH_3CN$ | 83 | 4 | 99 | 12 | 76 | 12 |
| 7 | $BF_3$ | $CH_3NO_2$ | 90 | 3 | 100 | <2 | 78 | 22 |
| 8 | XN-1010 | $CH_3CN$ | 83 | 7 | 95 | 35 | 38 | 27 |
| 9 | XN-1010 | $CH_3NO_2$ | 90 | 4 | 96 | 10 | 67 | 23 |
| 10 | A-15 | $CH_3NO_2$ | 90 | 4 | 99 | 8 | 68 | 24 |

XN-1010 = AMBERLYST X-1010 sulfonic acid resin;
A-15 = AMBERLYST-A15 sulfonic acid resin; both are products of Rohm and Haas Co.
Examples 8 and 10 used 2.0 g of resin; Example 9 used 1.0 g of resin.

As shown in Table 2, excellent conversions and good selectivity to the dicarbamate products are achieved with both boron trifluoride and sulfonic acid resins when a polar aprotic solvent is used. Nitromethane gives better selectivity to the dicarbamate compared with acetonitrile when a sulfonic acid resin is used (Compare Examples 9 and 10 with Example 8).

COMPARATIVE EXAMPLE 11
Preparation of Aliphatic Urethanes from Xylenes
Phosphoric Acid Solvent The procedure of U S. Pat. No. 4,879,410 (Example 22 of this reference) was followed. Thus, m-xylene, paraformaldehyde, methyl carbamate, and phosphoric acid were combined in a molar ratio of 1:2:2.5:7.5. Phosphoric acid was thus used as both a catalyst and solvent. The mixture was heated at 70° C. for 18 h. The acidic mixture was extracted several times with dichloromethane. The combined extracts were concentrated and analyzed by gas and liquid chromatography. The GC results indicated complete conversion of the m-xylene. The percent yields of dicarbamate (30%) and monocarbamate (3%) were determined by HPLC. The results are summarized in Table 3.

EXAMPLES 12 AND 13
Preparation of Aliphatic Urethanes from Xylenes
Nitromethane Solvent--$BF_3$ Catalyst Boron trifluoride etherate (1.50 g) was added to a stirred solution of methylene bis(methyl carbamate) (32.4 g) in nitromethane (100 mL) at 90° C. m-Xylene (6.70 g) was added dropwise over about 15 min. The progress of the reaction was monitored by GC and HPLC. After 6 hours, 96% conversion of the m-xylene was achieved. By HPLC, the percent yields of dicarbamate (40%) and monocarbamate (54%) were found. Only 6% of the original m-xylene was not recoverable as useful products.

When o-xylene was used instead of m-xylene in an experiment run in the same way, conversion was 85% after 6 hours. The observed selectivities were: dicarbamate (34%); monocarbamate (58%). About 8% of the original o-xylene was not recoverable. The results of these experiments appear in Table 3.

TABLE 3

Preparation of Aliphatic Urethanes from Xylenes
Nitromethane versus Phosphoric Acid as Solvent

| Ex | Cat. | Solvent | Temp (°C.) | Time (h) | Percent Conv. | Selectivity Monocarb | Dicarb | Amount Lost (%) |
|---|---|---|---|---|---|---|---|---|
| C11 | $H_3PO_4$ | $H_3PO_4$ | 70 | 18 | 100 | 3 | 30 | 67 |
| 12 | $BF_3$ | $CH_3NO_2$ | 90 | 6 | 94 | 54 | 40 | 6 |
| 13 | $BF_3$ | $CH_3NO_2$ | 90 | 6 | 85 | 58 | 34 | 8 |

Although moderate yields of dicarbamate are obtained with either phosphoric acid or the $BF_3$/nitromethane system, the amount of xylene that cannot be accounted for is much greater when phosphoric acid is used (67% versus about 7%). With the polar aprotic solvent, more than 90% of the xylene is converted either to the desired dicarbamate, or to monocarbamate which can be recovered by vacuum distillation or other techniques and further alkylated to give additional dicarbamate.

EXAMPLE 14

Preparation of Aliphatic Urethanes from Diphenyl Ether

Diphenyl ether (7 mmol) was combined with methylene bis(methyl carbamate) (21 mmol) in nitromethane (25 mL), and the mixture was heated to 90° C. Boron trifluoride etherate (0.14 g) was added, and the mixture was allowed to react at 90° C. for 6 hours. Conversion of the diphenyl ether was 96%. The observed selectivities were: monocarbamate (28%); dicarbamate (64%). Of the dicarbamate products, the 4,4'-isomer was 70% of the total as shown by proton and carbon-13 NMR spectroscopy.

EXAMPLE 15

Cracking of Anisole Dicarbamate to Diisocyanate

A 3-neck round-bottom flask was equipped with a reflux condenser, nitrogen inlet, and overhead trap for collecting volatile reaction products. Live steam was maintained in the reflux condenser. The reaction flask was charged with diphenyl ether (solvent) (25 g) and zinc powder (0.050 g), and was heated to 250° C. Nitrogen flow through the solution was regulated to about 5 mL/minute.

A solution of the anisole dicarbamate product of Example 7 was added as a 20 wt. % solution in diphenyl ether to the reaction flask slowly using a syringe pump over a 2-hour period. Following addition of the dicarbamate solution, the reaction mixture was refluxed for 1 hour. Analysis by gas chromatography showed complete conversion of the dicarbamate, with 90% selectivity to the desired diisocyanate product. The remaining product (10%) was the half-cracked material (monocarbamate-monoisocyanate).

We claim:

1. An aliphatic urethane of the formula:

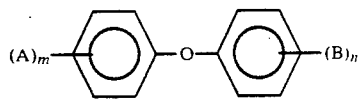

in which each of A and B separately represents a

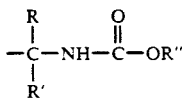

R and R', which may be the same or different, are selected from the group consisting of hydrogen, $C_1$-$C_{30}$ alkyl, alkenyl, aryl, and aralkyl;
R" is a $C_1$-$C_{10}$ alkyl or aryl group; and
m and n, which may be the same or different, are integers from 1 to 3.

2. The urethane of claim 1 wherein R and R' are hydrogen, R" is selected from the group consisting of methyl and ethyl, m=1, and n=1.

3. A process for producing an aryl-substituted alkyl urethane comprising reacting an aromatic ring-containing compound having at least one aromatic-ring hydrogen atom with an alkylene bis(carbamic acid ester) of the formula:

RCR'(NHCOOR")$_2$ in the presence of an acidic catalyst and a polar aprotic solvent selected from the group consisting of $C_1$-$C_{10}$ aliphatic and aromatic nitriles, amides, phosphoramides, nitro compounds, sulfones, and sulfoxides, to replace at least one aromatic-ring hydrogen atom of said aromatic ring-containing compound with a

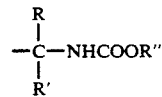

group to produce the aryl-substituted alkyl urethane;
wherein R and R', which may be the same or different, are selected from the group consisting of hydrogen, $C_1$-$C_{30}$ alkyl, alkenyl, aryl, and aralkyl; and R" is selected from the group consisting of $C_1$-$C_{10}$ alkyl and aryl; and
wherein the aromatic ring-containing compound is optionally substituted with one or more monovalent radicals selected from the group consisting of hydroxy, $C_1$-$C_{30}$ alkyl, alkaryl, aryl, amino, alkylthio, trialkylsilyl, acylamino, alkoxy, and alkyoxyalkyl.

4. The process of claim 3 wherein the aromatic ring-containing compound is selected from:

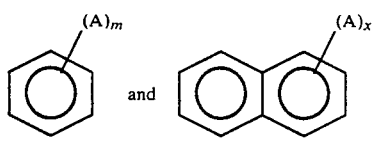

and the resulting aryl-substituted alkyl urethane is selected from:

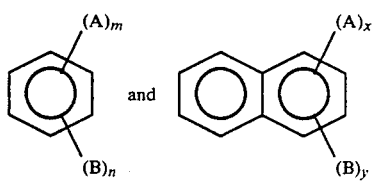

in which B represents a

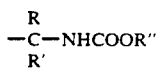

group;

A is a monovalent radical selected from the group consisting of hydroxy, $C_1$-$C_{30}$ alkyl, alkaryl, aryl, acylamino, amino, alkylthio, trialkylsilyl, alkoxy, and alkoxyalkyl;

m is an integer from 0 to 5;

n is an integer from 1 to 3;

n+m is less than or equal to 6;

x is an integer from 0 to 7;

y is an integer from 1 to 4; and x+y is less than or equal to 8.

5. The process of claim 3 wherein the aromatic ring-containing compound is selected from the group consisting of benzene, toluene, xylenes, ethylbenzene, diphenylmethane, anisole, ethyl phenyl ether, diphenyl ether, tert-butylbenzene, biphenyl, bisphenol-A, and phenol.

6. The process of claim 3 wherein R and R' are selected from the group consisting of hydrogen, methyl, ethyl, phenyl, methylphenyl, vinyl, and alkylvinyl.

7. The process of claim 3 wherein the acidic catalyst is selected from the group consisting of protic acids, Lewis acids, and solid acids.

8. The process of claim 3 wherein the polar aprotic solvent is selected from the group consisting of acetonitrile, propionitrile, benzonitrile, nitromethane, nitrobenzene, dimethyl sulfoxide, sulfolane, N-methyl-2-pyrrolidone, N,N-dimethylformamide, and nitroethane.

9. The process of claim 3 wherein said aryl-substituted alkyl urethane is catalytically hydrogenated to produce a cycloalkyl-substituted alkyl urethane.

10. The process of claim 3 wherein the alkylene bis(carbamic acid ester) is replaced by a mixture of a formaldehyde or acetaldehyde source and a carbamic acid ester of the formula $H_2N$—COOX, wherein X represents a $C_1$-$C_{10}$ alkyl, aryl, or aralkyl group.

11. A process for producing an aryl-substituted alkyl isocyanate, said process comprising:

(a) reacting an aromatic ring-containing compound having at least one aromatic-ring hydrogen atom with an alkylene bis(carbamic acid ester) of the formula:

$$RCR'(NHCOOR'')_2$$

in the presence of an acidic catalyst and a polar aprotic solvent selected from the group consisting of $C_1$-$C_{10}$ aliphatic and aromatic nitriles, amides, phosphoramides, nitro compounds, sulfones, and sulfoxides, to replace at least one aromatic-ring hydrogen atom of said aromatic ring-containing compound with a

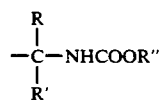

group to produce the aryl-substituted alkyl urethane;

wherein R and R', which may be the same or different, are selected from the group consisting of hydrogen, $C_1$-$C_{30}$ alkyl, alkenyl, aryl, and aralkyl; and R" is selected from the group consisting of $C_1$-$C_{10}$ alkyl and aryl; and wherein the aromatic ring-containing compound is optionally substituted with one or more monovalent radicals selected from the group consisting of hydroxy, $C_1$-$C_{30}$ alkyl, alkaryl, aryl, amino, alkylthio, trialkylsilyl, acylamino, alkoxy, and alkoxyalkyl; and (b) heating said aryl-substituted alkyl urethane in the vapor phase or in a high-boiling solvent to thermally convert the

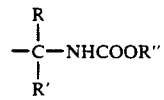

substituents of the aryl-substituted alkyl urethane to

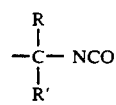

groups to produce an aryl-substituted alkyl isocyanate.

12. The process of claim 11 wherein the aromatic ring-containing compound is selected from:

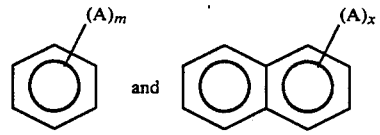

and the resulting aryl-substituted alkyl isocyanate is selected from:

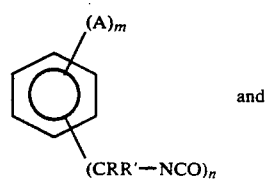

-continued

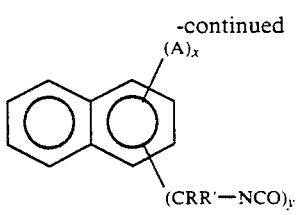

wherein A is a monovalent radical selected from the group consisting of hydroxy, $C_1$-$C_{30}$ alkyl, alkaryl, aryl, acylamino, amino, alkylthio, trialkylsilyl, alkoxy, and alkoxyalkyl;

m is an integer from 0 to 5;
n is an integer from 1 to 3;
n+m is less than or equal to 6;
x is an integer from 0 to 7;
y is an integer from 1 to 4; and
x+y is less than or equal to 8.

13. The process of claim 11 wherein the aromatic ring-containing compound is selected from the group consisting of benzene, toluene, xylenes, ethylbenzene, diphenylmethane, anisole, ethyl phenyl ether, diphenyl ether, tert-butylbenzene, biphenyl, bisphenol-A, and phenol.

14. The process of claim 11 wherein R and R' are selected from the group consisting of hydrogen, methyl, ethyl, phenyl, methylphenyl, vinyl, and alkylvinyl.

15. The process of claim 11 wherein the acidic catalyst is selected from the group consisting of boron trifluoride compounds and sulfonic acid resins.

16. The process of claim 11 wherein the polar aprotic solvent is selected from the group consisting of acetonitrile, propionitrile, benzonitrile, nitromethane, nitrobenzene, dimethyl sulfoxide, sulfolane, N-methyl-2-pyrrolidone, N,N-dimethylformamide, and nitroethane.

17. The process of claim 11 wherein the acidic catalyst is removed from the aryl-substituted alkyl urethane prior to step (b).

18. The process of claim 11 wherein the aromatic ring-containing compound is anisole, the alkylene bis(carbamic acid ester) is methylene bis(methylcarbamate), the acidic catalyst is boron trifluoride etherate, and the polar aprotic solvent is nitrile.

19. The process of claim 4 wherein the aryl-substituted urethane is catalytically hydrogenated, and the resulting cycloalkyl-substituted alkyl urethane is heated in the vapor phase or in a high-boiling solvent, optionally in the presence of a promoter, to thermally convert the

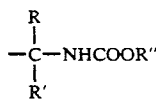

substituents of the cycloalkyl-substituted alkyl urethane to

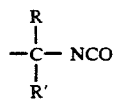

groups to produce a cycloalkyl-substituted alkyl isocyanate.

20. The process of claim 11 wherein the alkylene bis(carbamic acid ester) is replaced by a mixture of a formaldehyde or acetaldehyde source and carbamic acid ester of the formula, $H_2N$-COOX, wherein X represent a $C_1$-$C_{10}$ alkyl, aryl, or aralkyl group.

21. A process for producing an aryl-substituted alkyl urethane selected from:

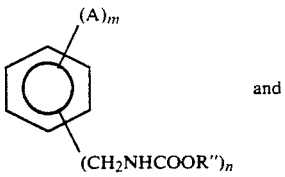

and

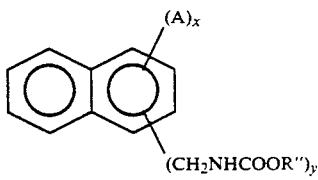

said process comprising reacting an aromatic ring-containing compound selected from:

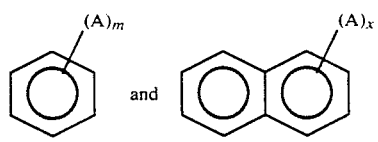

with a methylene bis(carbamic acid ester) of the formula:

$CH_2(NHCOOR'')_2$ in the presence of an acidic catalyst selected from Lewis acids and sulfonic acid resins, and a polar aprotic solvent selected from the group consisting of $C_1$-$C_{30}$ aliphatic and aromatic nitriles, amides, phosphoramides, and sulfoxides, to produce the aryl-substituted alkyl urethane;

wherein A is a monovalent radical selected from the group consisting of halogen, hydroxy, amino, $C_1$-$C_{30}$ alkyl, alkaryl, amino, alkylthio, trialkylsilyl, aryl, acylamino, alkoxy, and alkoxyalkyl;
R'' is selected from the group consisting of methyl and ethyl;
m is an integer from 0 to 5;
n is an integer from 1 to 3;
n+m is less than or equal to 6;
x is an integer from 0 to 7;
y is an integer from 1 to 4; and
x+y is less than or equal, to 8.

22. The process of claim 21 wherein the aromatic ring-containing compound is selected from the group consisting of benzene, toluene, xylenes, ethylbenzene, diphenylmethane, anisole, ethyl phenyl ether, diphenyl ether, tert-butylbenzene, biphenyl, bisphenol-A, and phenol.

23. The process of claim 21 wherein the acidic catalyst is a boron trifluoride compound.

24. The process of claim 21 wherein the polar aprotic solvent is selected from the group consisting of acetonitrile, propionitrile, benzonitrile, nitromethane, nitrobenzene, N-methyl-2-pyrrolidone, N,N-dimethylformamide, sulfolane, dimethyl sulfoxide, and nitroethane.

25. The process of claim 21 comprising heating the aryl-substituted alkyl urethane in the vapor phase or in a high-boiling solvent, optionally in the presence of a promoter, to thermally convert the aryl-substituted alkyl urethane to an aryl-substituted alkyl isocyanate selected from:

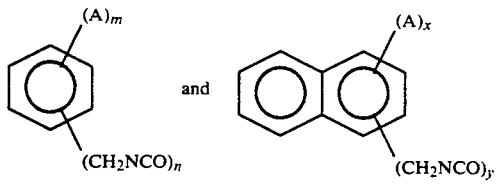

26. The process of claim 21 comprising:
(a) catalytically hydrogenating the aryl-substituted alkyl urethane to produce a cycloalkyl-substituted alkyl urethane; and
(b) heating the cycloalkyl-substituted alkyl urethane in the vapor phase or in a high-boiling solvent, optionally in the presence of a promoter, to thermally convert the cycloalkyl-substituted alkyl urethane to a cycloalkyl-substituted alkyl isocyanate selected from:

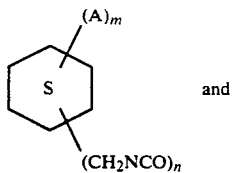

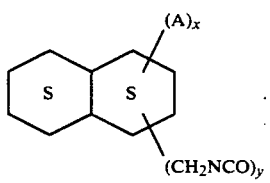

* * * * *